US007264825B2

(12) United States Patent (10) Patent No.: US 7,264,825 B2
Vogt et al. (45) Date of Patent: Sep. 4, 2007

(54) PHARMACEUTICAL PREPARATION WITH RETARDING ACTIVE INGREDIENT RELEASE, METHOD FOR ITS PRODUCTION AND ITS USE

(75) Inventors: Sebastian Vogt, Erfurt (DE); Matthias Schnabelrauch, Jena (DE); Klaus-Dieter Kühn, Marburg (DE)

(73) Assignee: Herseus Kulzer GmbH, Hanau (DE)

( * ) Notice: Subject to any disclaimer, the term of this patent is extended or adjusted under 35 U.S.C. 154(b) by 487 days.

(21) Appl. No.: 10/600,557

(22) Filed: Jun. 20, 2003

(65) Prior Publication Data

US 2004/0052841 A1   Mar. 18, 2004

(30) Foreign Application Priority Data

Jun. 21, 2002   (DE) ................. 102 27 914

(51) Int. Cl.
*A61J 9/14* (2006.01)
(52) U.S. Cl. ...................... 424/489; 424/400
(58) Field of Classification Search ............... None
See application file for complete search history.

(56) References Cited

U.S. PATENT DOCUMENTS 4,283,799 A * 8/1981 Pratt et al. ............... 623/23.37

4,588,583 A * 5/1986 Pietsch et al. ............... 523/116
5,797,873 A * 8/1998 Franz et al. ................ 604/500
2002/0004071 A1   1/2002 Cherukuri ................... 424/486

FOREIGN PATENT DOCUMENTS

EP          0 611 571 A1    8/1994
WO       WO 02/09783 A1    2/2002

OTHER PUBLICATIONS

Salaria, M. Indian Pediatrics Apr. 2001; 38:372-375, downloaded from the world wide web at www.indianpediatrics.net/april2001/april-372-375.htm on Jun. 14, 2006.*

* cited by examiner

*Primary Examiner*—Michael P. Woodward
*Assistant Examiner*—Eric E. Silverman
(74) *Attorney, Agent, or Firm*—Norris McLaughlin & Marcus PA

(57) ABSTRACT

The invention describes pharmaceutical preparations with retarding active ingredient release, which consist of mixtures of powdery teicoplanin and at least one powdery, water soluble salt form of gentamicin, clindamycin, kanamycin, amikacin, tobramycin, vancomycin, moxifloxacin and ciprofloxacin and an inorganic and/or organic adjuvant. The pharmaceutical preparations are used as permanent or as temporary implants in the form of tablets, molded bodies, fibers and granules.

10 Claims, No Drawings

PHARMACEUTICAL PREPARATION WITH RETARDING ACTIVE INGREDIENT RELEASE, METHOD FOR ITS PRODUCTION AND ITS USE

The present invention relates to a pharmaceutical preparation with retarding active ingredient release as resorbable and also as non-resorbable implants in human and veterinary medicine for the treatment of severe, local bacterial infections in hard and soft tissues. The pharmaceutical preparation in particular shall be used in the therapy of bacterial infections, which due to resistance appearances are no longer accessible with a simple local antibiotic treatment with only one antibiotic. The invention furthermore relates to a method for the production and the use of the preparation.

The treatment of local microbial infections of hard and soft tissues in human and veterinary medicine requires high local concentrations of antibiotics in the infected tissue area. It has been known for quite some time that the systemic application of antibiotics is associated with a series of problems. The systemic application often requires the use of very high doses of antibiotics in order to achieve antimicrobially effective antibiotics concentrations in the infected tissue. Thus, particularly with the use of aminoglycoside antibiotics, severe damage to the organism can occur due to their nephro-and oto-toxicity. It has therefore been suggested to use antibiotics in topical release systems, or transfer them into suitable controlled-release preparations. It is furthermore useful if the topical release systems exhibit a high level of active ingredient release during the first few hours and subsequently over the course of several days release a continuous low level of active ingredient quantities to largely achieve that the bacterial pathogens are killed.

Teicoplanin is a glycopeptide antibiotic, which is effective towards Gram-positive bacterial germs. It inhibits mureic synthesis and thus cross-linkage of the bacterial cell walls. Teicoplanin is especially beneficial in that it has a considerably higher shelf life than β-lactam antibiotics and that it can be used for patients that are allergic to penicillin. Aminoglycoside antibiotics, such as gentamicin and kanamycin, and also clindamycin impair bacterial protein synthesis and thus have a bactericidal effect with many Gram-positive bacteria, anaerobic bacteria and in part also with Gram-negative bacteria. Fluor-quinolone antibiotics, such as ciprofloxacin and moxifloxacin, represent broad-band antibiotics and act as topoisomerase inhibitors and as gyrase inhibitors against a variety of Gram-positive bacteria. In the treatment of problematic germs it is therefore useful to combine two antibiotics, which have different attack methods in the bacterial metabolism, with each other. This increases the probability of an effective treatment of this problematic germs.

EP 0 611 571 reveals a topical medication with delayed release in the form of a dry product or a suspension, in an inert liquid carrier, containing the combination of teicoplanin and another medication with alkaline character as the hardly water soluble product. As the alkalene medication the aminoglycosides gentamicin, netilmicin and tobramycin are mentioned. In this disclosure document, hardly soluble reaction products made of teicoplanin with gentamicin, teicoplanin with netilmicin as well as teicoplanin with tobramycin are claimed, which are used as topical medications in the form of dry products or a suspension.

Until now no publications are known which describe pharmaceutical preparations that consist of mixtures of powdery teicoplanin and powdery water soluble salts of gentamicin, clindamycin, kanamycin, amikacin, tobramycin, vancomycin, moxifloxacin and ciprofloxacin and suitable inorganic and/or organic adjuvants and that exhibit a delayed active ingredient release effect in an aqueous environment.

The invention is based on the task of developing a pharmaceutical preparation that contains teicoplanin and other antibiotics and that releases the antibiotics over a period of several days in a delayed effect in an aqueous environment, such as under physiological conditions.

The task is resolved pursuant to the present invention through the features of the broad and preferred descriptions hereinbelow.

The invention is based on the surprising finding that mixtures consisting of powdery teicoplanin and at least one powdery, water soluble salt of at least one of gentamicin, clindamycin, kanamycin, amikacin, tobramycin, vancomycin, moxifloxacin and ciprofloxacin exhibit a delayed active ingredient release in an aqueous environment in the presence of suitable inorganic adjuvants and/or organic adjuvants. It is surprising that contrary to EP 0 611 571, where slightly water soluble adducts of the teicoplanin and other antibiotics are used as medications, in the invented pharmaceutical preparation no synthesis of hardly soluble teicoplanin antibiotics adducts is required and that nevertheless a delayed release of antibiotics of the invented pharmaceutical preparation in an aqueous environment is found. The pharmaceutical preparation can be produced in the conventional manner for pharmaceutics, as in EP 0 611 571. The pharmaceutical preparation is furthermore suited for several combinations made of teicoplanin and other antibiotics. The pharmaceutical preparation can be accomplished with various adjuvants in tablet form.

Pursuant to the invention it is preferred that calcium carbonate, calcium sulfate dihydrate, tri-calcium phosphate and hydroxylapatite are used as the inorganic adjuvants.

It is furthermore beneficial pursuant to the invention that polyesters of the lactic acid, glycolic acid, 5-hydroxy valeric acid and 6-hydroxy caproic acid are used as organic adjuvants as well as their co-polymers are organic adjuvants.

It is preferred that the mixtures are formed through pressing, extrusion, spinning and granulation into tablets, molded bodies, fibers and granules.

It is furthermore beneficial that a combination of polymerizable methacrylic acid esters and mixtures consisting of powdery teicoplanin and powdery, water soluble salts of gentamicin, clindamycin, kanamycin, amikacin, tobramycin, vancomycin, moxifloxacin and ciprofloxacin is polymerized into a molded body. Pursuant to the invention these are in particular balls or cylindrical bodies consisting of polymeric methacrylic acid esters, which contain the invented mixtures of powdery teicoplanin and at least one powdery, water soluble salt form of gentamicin, clindamycin, kanamycin, amikacin, tobramycin, vancomycin, moxifloxacin and ciprofloxacin, and can be used as implantable active ingredient carriers, similar to the Septopal® chains, for local infection treatment purposes. It is also in accordance with the invention that the invented mixtures of powdery teicoplanin and at least one powdery, water soluble salt form of gentamicin, clindamycin, kanamycin, amikacin, tobramycin, vancomycin, moxifloxacin and ciprofloxacin can be contained in bone cements. The term molded bodies should also be interpreted as cured bone cements.

Pursuant to the invention the mixtures consisting of powdery teicoplanin and powdery, water soluble salts of gentamicin, clindamycin, kanamycin, amikacin, tobramycin, vancomycin, moxifloxacin and ciprofloxacin can be admixed to inorganic calcium phosphate bone cements before said cements are cured. It is also pursuant to the invention that the mixtures are used in self-curing calcium sulfate mixtures for filling in bone defects.

It is useful that the mixtures are part of resorbable and non-resorbable coatings, which are applied to non-metallic and metallic implants.

Pursuant to the invention the pharmaceutical preparation shall be used in the form of tablets, molded bodies, fibers and granules as permanent implants and as temporary implants.

The invention shall be explained in the following through the examples 1 through 3 in more detail, however without limiting the invention.

EXAMPLE 1

A mixture of 500.0 mg calcium sulfate dihydrate (Fluka), 125.0 mg poly-L-lactide (M-10,000 g/mol), 18.7 mg gentamicin sulfate (AK 628) and 18.7 mg teicoplanin is ground together. 200 mg of this mixture, respectively, are pressed in a press at a pressure of 5 tons within a period of two minutes to disk-shaped molded bodies with a diameter of 13 mm.

EXAMPLE 2

A mixture of 500.0 mg calcium sulfate dihydrate (Fluka), 125.0 mg poly-L-lactide (M-10,000 g/mol), 18.7 mg clindamycin hydrochloride and 18.7 mg teicoplanin is ground together. 200 mg of this mixture, respectively, are pressed in a press at a pressure of 5 tons within a period of two minutes to disk-shaped molded bodies with a diameter of 13 mm.

EXAMPLE 3

A mixture of 1,000.0 mg calcium sulfate dihydrate (Fluka), 250.0 mg poly-L-lactide (M-10,000 g/mol), 18.7 mg kanamycin sulfate (Fluka) and 18.7 mg teicoplanin is ground together. 200 mg of this mixture, respectively, are pressed in a press at a pressure of 5 tons within a period of two minutes to disk-shaped molded bodies with a diameter of 13 mm.

Antibiotics Release Experiments

The molded bodies produced in the examples 1-3 were introduced into Sërensen buffer with pH 7.4 and stored in it at 37° C. over a period of 12 days. Sampling took place on a daily basis, wherein the release medium was replaced. The release of antibiotics from the molded bodies was traced with an agar diffusion test while employing bacillus subtilis ATCC 6633 as the test germ. The inhibiting areola diameter was determined with the aid of a scanner and evaluated with special evaluation software. The results are depicted in the table.

TABLE

Results of the microbial agar diffusion test used to determine the release of antibiotics from the molded bodies from examples 1-3 in dependency upon the storage time of the sample bodies in the Sörensen buffer at 37° C.

| | Example 1 | | Example 2 | | Example 3 | |
|---|---|---|---|---|---|---|
| Time [d] | Dilution | Inhibiting Areola Diameter [mm] | Dilution | Inhibiting Areola Diameter [mm] | Dilution | Inhibiting Areola Diameter [mm] |
| 1 | 1:100 | 22.40 | 1:100 | 20.00 | 1:70 | 20.35 |
| 2 | 1:15 | 20.85 | 1:30 | 20.80 | 1:5 | 21.15 |
| 3 | 1:3 | 20.28 | 1:14 | 19.80 | Undiluted | 21.45 |
| 6 | Undiluted | 18.25 | Undiluted | 21.55 | Undiluted | 14.20 |
| 9 | Undiluted | 15.63 | Undiluted | 18.35 | Undiluted | Not determined |
| 12 | Undiluted | 17.70 | undiluted | 21.30 | Undiluted | 15.25 |

What is claimed is:

1. A dry pharmaceutical preparation comprising a dry mixture of powdery teicoplanin and at least one powdery, water soluble salt form of at least one of gentamicin, clindamycin, kanamycin, amikacin, tobramycin, vancomycin, moxifloxacin and ciprofloxacin and an inorganic and/or organic adjuvant.

2. The dry pharmaceutical preparation pursuant to claim 1, which contains calcium carbonate, calcium sulfate dihydrate, tricalcium phosphate and/or hydroxylapatite as the inorganic adjuvant.

3. The dry pharmaceutical preparation pursuant to claim 1, which contains polyesters of at least one of lactic acid, glycolic acid, 5-hydroxy valeric acid, 6-hydroxy caproic acid and co-polymers thereof as organic adjuvants.

4. The dry pharmaceutical preparation pursuant to claim 1, which is in the form of one of tablets, molded bodies, fibers and granules.

5. The dry pharmaceutical preparation pursuant to claim 1, comprising a combination of polymerizable methacrylic acid esters and mixtures consisting of powdery teicoplanin and at least one powdery, water soluble salt form of at least one of gentamicin, clindamycin, kanamycin, amikacin, tobramycin, vancomycin, moxifloxacin and ciprofloxacin formed and polymerized into a molded body.

6. The dry pharmaceutical preparation pursuant to claim 1, wherein the mixture is part of a resorbable and/or of non-resorbable coating, which has been applied to non-metallic and metallic implants.

7. The dry pharmaceutical preparation pursuant to claim 1, wherein before being cured inorganic calcium phosphate bone cements and plaster mixtures are admixed to mixtures consisting of powdery teicoplanin and at least one powdery, water soluble salt form of at least one of gentamicin, clindamycin, kanamycin, amikacin, tobramycin, vancomycin, moxifloxacin and/or ciprofloxacin.

8. A permanent or temporary implant comprising a dry pharmaceutical preparation pursuant to claim 1 in the form of one of tablets, molded bodies, fibers and granules.

9. A method of treating a bacterial infection in a patient in need thereof comprising administering to said patient a pharmaceutical preparation pursuant to claim 1.

10. A method of preparing the dry pharmaceutical preparation according to claim 1, said method comprising dry mixing powdery teicoplanin and at least one powdery, water soluble salt form of at least one of gentamicin, clindamycin, kanamycin, amikacin, tobramycin, vancomycin, moxifloxacin and ciprofloxacin and an inorganic and/or organic adjuvant.

* * * * *